United States Patent
Smith

(10) Patent No.: US 9,056,121 B1
(45) Date of Patent: *Jun. 16, 2015

(54) METHOD OF ADMINISTERING HYALURONAN FORMULATION FOR THE AMELIORATION OF OSTEOPHYTES

(75) Inventor: James D. Smith, Lexington, KY (US)

(73) Assignee: Reyn Pharma, LLC, Lexington, KY (US)

(*) Notice: Subject to any disclaimer, the term of this patent is extended or adjusted under 35 U.S.C. 154(b) by 506 days.

This patent is subject to a terminal disclaimer.

(21) Appl. No.: 13/417,817

(22) Filed: Mar. 12, 2012

Related U.S. Application Data

(63) Continuation-in-part of application No. 12/485,265, filed on Jun. 16, 2009, now Pat. No. 8,163,716.

(60) Provisional application No. 61/076,999, filed on Jun. 30, 2008.

(51) Int. Cl.
*A61K 31/728* (2006.01)

(52) U.S. Cl.
CPC .................................... *A61K 31/728* (2013.01)

(58) Field of Classification Search
CPC ....................................................... A61K 31/72
See application file for complete search history.

(56) References Cited

U.S. PATENT DOCUMENTS

| | | | | |
|---|---|---|---|---|
| 6,476,005 B1 * | 11/2002 | Petito et al. | ..................... | 514/62 |
| 6,607,745 B2 * | 8/2003 | Leneau | ......................... | 424/439 |
| 6,924,273 B2 * | 8/2005 | Pierce | ............................. | 514/54 |
| 6,979,679 B2 * | 12/2005 | Marcum | ........................ | 514/53 |
| 8,163,716 B1 * | 4/2012 | Smith | ............................ | 514/54 |
| 2002/0173484 A1 * | 11/2002 | Leneau | ........................... | 514/54 |
| 2010/0055053 A1 * | 3/2010 | Ripley et al. | .................... | 424/49 |

OTHER PUBLICATIONS

"Bone Spurs", downloaded from MayoClinic.com, revised Jan 5, 2010, pp. 1-6.*
Kim et al., "Therapeutic Effect of Hyaluronic Acid on Experimental Osteoarthritis of Ovine Temporomandibular Joint" J. Vet. Med. Sci. (2001) vol. 63 No. 10, pp. 1083-1089.*

* cited by examiner

*Primary Examiner* — Eric Olson
(74) *Attorney, Agent, or Firm* — Curatolo Sidoti Co., LPA; Salvatore A. Sidoti; Floyd Trillis, III

(57) ABSTRACT

Disclosed is a method for the amelioration of osteophyte formation including administering to a subject a therapeutically effective amount of an exogenous hyaluronan formulation.

29 Claims, 1 Drawing Sheet

FIGURE 1
FIGURE 2
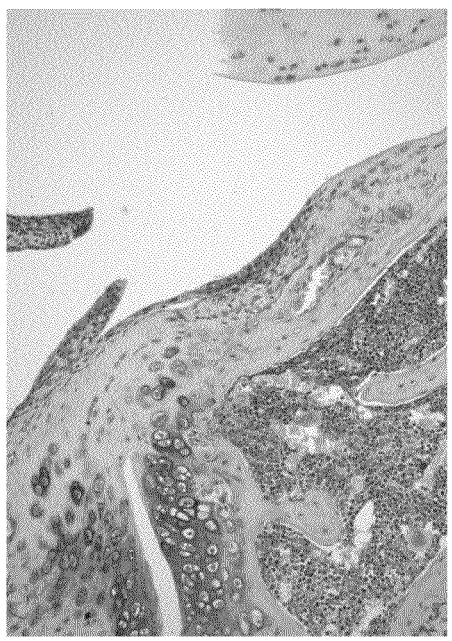
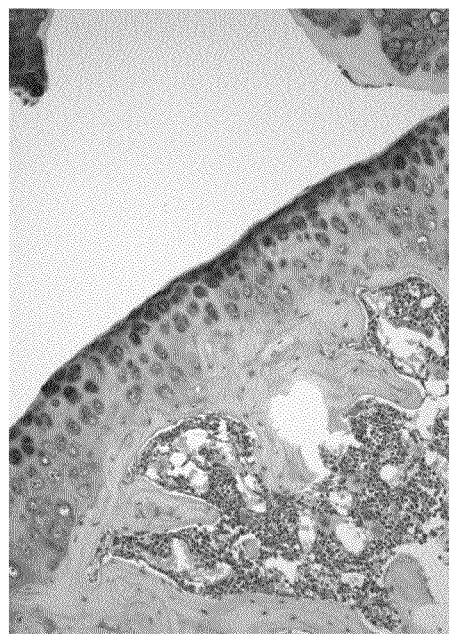

METHOD OF ADMINISTERING HYALURONAN FORMULATION FOR THE AMELIORATION OF OSTEOPHYTES

CROSS REFERENCE TO RELATED APPLICATIONS

This application is a continuation-in-part of U.S. application for patent Ser. No. 12/485,265 filed on Jun. 16, 2009, which claims the benefit of the filing date under 35 U.S.C. §119(e) of U.S. Provisional Application for patent Ser. No. 61/076,999 filed on Jun. 30, 2008, both of which are hereby incorporated by reference.

TECHNICAL FIELD

The present disclosure relates to a method of administering a composition comprising a therapeutically effective amount of an exogenous hyaluronan to a vertebrate subject for preventing, slowing, attenuating, mitigating, and/or ameliorating the formation of osteophytes in bone remodeling in the subject.

BACKGROUND

Osteophytes, commonly called bone spurs, are bony projections that develop along the edges of bones. They may form on any bone including vertebrae, and often form where bones meet at joints. Osteophytes may also develop where ligaments and tendons connect to bone. Range of motion is frequently limited in the affected joint and although osteophytes themselves are not painful, they frequently rub against nerves and cause pain. All vertebrate species are subject to the development of osteophytes.

Osteophyte formation has been classically related to any sequential and consequential changes in bone formation due to aging, degeneration, mechanical instability, and disease. For forty-two percent of the adult human population, degeneration and development of osteophytes will lead to symptoms of neck and back pain, radiating arm and leg pain, and weakness in the extremities during their lifetime.

Medical treatments for osteophytes are typically palliative and not directed at the underlying problem. Osteophytes that limit range of motion or cause other problems that limit ability may require surgery to prevent further joint damage. Surgical options are determined by the location of the osteophyte. Osteophytes are often removed as part of a more comprehensive surgery for osteoarthritis. For example, with osteoarthritis in an elbow the surgeon may remove osteophytes while making other repairs to the joint. Access to the joint for removal of osteophytes may be via arthroscopic surgery or with an open procedure.

There is no teaching in the art of a method for preventing, slowing, attenuating, mitigating, and/or ameliorating the formation of osteophytes in bone remodeling in a vertebrate subject by administering a composition comprising a therapeutically effective amount of an exogenous hyaluronan to the subject. The present disclosure provides such a method.

SUMMARY

Disclosed is a method for preventing, slowing, attenuating, mitigating, and/or ameliorating the formation of osteophytes in bone remodeling in a vertebrate subject, the method comprising administering a composition comprising a therapeutically effective amount of an exogenous hyaluronan formulation to the vertebrate subject.

BRIEF DESCRIPTION OF THE DRAWINGS

FIG. 1 is a photograph of the histopathology tissue section of Control Mouse 1.

FIG. 2 is a photograph of the histopathology tissue section of Treatment Mouse 2.

DETAILED DESCRIPTION

Disclosed is a method of administering a modified hyaluronan biopolymer to a vertebrate subject for the purposes of preventing, slowing, attenuating, mitigating, and/or ameliorating the formation of osteophytes. The method comprises administering a composition comprising a therapeutically effective amount of exogenous hyaluronan biopolymer to the subject.

The method of administering a therapeutically effective amount of the hyaluronan biopolymer to a subject may be accomplished by any means known in the art, such as, without limitation, by administering by oral or parenteral routes of administration. According to certain illustrative embodiments, parenteral administration of the therapeutically effective amount of the hyaluronan may comprise subcutaneous administration, intramuscular administration, and intravenous administration.

According to certain illustrative embodiments, and without limitation, therapeutically effective amounts of the hyaluronan biopolymer which may be administered to a subject in need thereof may comprise from about 0.2 to about 5 mg per kg body weight of the subject per day, from about 0.4 to about 4 mg per kg body weight of the subject per day, from about 0.6 to about 3 mg per kg body weight of the subject per day, from about 0.8 to about 2 mg per kg body weight of the subject per day, and about 1 mg per kg body weight of the subject per day. The daily therapeutically effective amount of the hyaluronan biopolymer may be administered to the subject as a single dose comprising the entire therapeutically effective amount. Alternatively, the therapeutically effective amount of the hyaluronan biopolymer may be achieved by administering in multiple lower amounts that cumulatively achieve the daily therapeutically effective amount.

The term "hyaluronan" as used herein refers to hyaluronic acid or any physiological salt form of hyaluronic acid. The hyaluronan biopolymer may be polydisperse and therefore may comprise a mixture of polymers having different molecular masses. In certain embodiments, the hyaluronan biopolymer is polydisperse and therefore comprises a mixture of polymers having different molecular masses.

Without limitation, the hyaluronan biopolymer that is administered to the vertebrate subject may comprise molecular weights in range from about 50,000 to about 8,000,000 Daltons. By way of illustration, suitable hyaluronan may comprise a mixture of polymers having different molecular masses from about 500,000 to about 2,500,000 Daltons, or from about 750,000 to about 2,250,000 Daltons, or from about 1,000,000 to about 2,000,000 Daltons, or from about 1,250,000 to about 1,750,000 Daltons, or from about 1,375,000 to about 1,625,000 Daltons. According to certain embodiments, the biopolymer comprises a weight average molecular weight of about 1,500,000 Daltons.

Without limitation, the physiological salt form of the hyaluronan biopolymer may comprise an alkali metal salt. For example, according to an illustrative embodiment, the physiological salt may comprise sodium hyaluronate.

According to illustrative embodiments, the biopolymer composition comprises a product of microbial fermentation. By producing the polymer by extra-cellular microbial fermentation, it is considered to be a vegan product. Accordingly, the hyaluronan may contain no animal derived materials, which minimizes the risk of transmission of animal spongiform encephalopathy. Producing the hyaluronan polymer by microbial fermentation also results in more consistent molecular profile, molecular weight and polydispersity that is optimized for oral bioavailability.

The hyaluronan composition also comprises a pharmaceutically acceptable carrier that is safe for human or veterinary consumption. Without limitation, and by way of example only, a suitable carrier for the hyaluronan composition is water.

The hyaluronan composition further comprises at least one pharmaceutically acceptable excipient. Without limitation, and by way of example only, a suitable excipient for the hyaluronan composition comprises sodium chloride.

The hyaluronan composition may have a pH that is between about 2.5 and about 7. According to certain illustrative embodiments, the hyaluronan composition hyaluronan composition may have a pH that is between about 3.5 and about 7. According to certain illustrative embodiments, the hyaluronan composition hyaluronan composition may have a pH that is between about 4.5 and about 7. According to certain illustrative embodiments, the hyaluronan composition hyaluronan composition may have a pH that is between about 5.5 and about 7. According to certain illustrative embodiments, the hyaluronan composition hyaluronan composition may have a pH that is between about 2.5 and about 5.5. According to further illustrative embodiments, the hyaluronan composition may have a pH that is between about 2.5 and about 4.5. According to further illustrative embodiments, the hyaluronan composition may have a pH that is between about 4.5 and about 5.5.

The hyaluronan composition may also include a pH altering agent. The pH altering agent may be included in the hyaluronan composition in an amount effective to provide a pH of the hyaluronan composition that is between about 2.5 and about 7.

The hyaluronan composition may also include a pH altering agent. The pH altering agent may be included in the hyaluronan composition in an amount effective to provide a pH of the hyaluronan composition that is between about 3.5 and about 7.

The hyaluronan composition may also include a pH altering agent. The pH altering agent may be included in the hyaluronan composition in an amount effective to provide a pH of the hyaluronan composition that is between about 4.5 and about 7.

The hyaluronan composition may also include a pH altering agent. The pH altering agent may be included in the hyaluronan composition in an amount effective to provide a pH of the hyaluronan composition that is between about 5.5 and about 7.

According to certain illustrative embodiments, the pH altering agent may be included in the hyaluronan composition in an amount effective to provide a pH of the hyaluronan composition that is between about 2.5 and about 5.5.

According to further illustrative embodiments, the pH altering agent may be included in the hyaluronan composition in an amount effective to provide a pH of the hyaluronan composition that is between about 2.5 and about 4.5.

According to further illustrative embodiments, the pH altering agent may be included in the hyaluronan composition in an amount effective to provide a pH of the hyaluronan composition that is between about 4.5 and about 5.5.

Without limitation, and by way of example only, a suitable pH altering agent for the hyaluronan composition comprises an organic acid such as citric acid. According to certain embodiments, and without limitation, citric acid is the pH altering agent and it is included in the hyaluronan composition in an amount effective to provide a pH of the hyaluronan composition that is between about 2.5 and about 7.

According to certain embodiments, and without limitation, citric acid is the pH altering agent and it is included in the hyaluronan composition in an amount effective to provide a pH of the hyaluronan composition that is between about 3.5 and about 7.

According to certain embodiments, and without limitation, citric acid is the pH altering agent and it is included in the hyaluronan composition in an amount effective to provide a pH of the hyaluronan composition that is between about 4.5 and about 7.

According to certain embodiments, and without limitation, citric acid is the pH altering agent and it is included in the hyaluronan composition in an amount effective to provide a pH of the hyaluronan composition that is between about 5.5 and about 7.

According to certain illustrative embodiments, the pH altering agent is citric acid and is included in the hyaluronan composition in an amount effective to provide a pH of the hyaluronan composition that is between about 2.5 and about 5.5.

According to certain illustrative embodiments, the pH altering agent is citric acid and is included in the hyaluronan composition in an amount effective to provide a pH of the hyaluronan composition that is between about 2.5 and about 4.5.

According to certain illustrative embodiments, the pH altering agent is citric acid and is included in the hyaluronan composition in an amount effective to provide a pH of the hyaluronan composition that is between about 4.5 and about 5.5.

According to certain illustrative embodiments, the composition comprises a therapeutically effective amount of hyaluronan and an antimicrobial preservative. Any known antimicrobial preservative that is generally regarded as safe for human or veterinary consumption may be included in the hyaluronan composition. Without limitation, suitable antimicrobial preservatives include potassium sorbate, sodium benzoate and mixtures thereof The biopolymer composition and method of administration may be useful for prevention of the formation of osteophytes in a wide variety of vertebrate species. For example, and by way of example only, the hyaluronan composition may be administered to any one of a human, an equine, a canine or a feline species.

The hyaluronan may be formulated into a wide variety of orally ingestible compositions. The hyaluronan may be formulated with an acceptable carrier to provide an orally ingestible liquid or a solid or semi-solid food product. Liquid forms include solutions, suspensions, emulsions, syrups and the like. According to certain illustrative embodiments, the hyaluronan composition may be formulated with an orally ingestible liquid carrier to provide an orally ingestible hyaluronan composition. For example, the hyaluronan may be formulated with an orally ingestible liquid carrier to provide a beverage, dietary supplement formulation, or nutritional supplement. The beverages, dietary supplements and nutritional supplements may be provided ready for oral ingestion or may be provided in a concentrate that requires dilution with acceptable liquids prior to oral ingestion. According to alternative embodiments, the hyaluronan may be formulated into other orally ingestible product forms, such as powders, pills, lozenges, tablets, caplets, capsules, liquid capsules, gel capsules and the like. Flavoring agents may also be added to the hyaluronan compositions to provide a more palatable orally ingestible composition.

The orally administrable hyaluronan composition may further include nutritionally effective amounts of an additional supplement. According to certain embodiments, the hyaluronan composition further comprises nutritionally effective amounts of at least one vitamin, or at least one mineral or a combination of at least one vitamin and at least one mineral. According to certain embodiments, the hyaluronan composition comprises a therapeutically effective amount of hyaluronan and a nutritionally effective amount of at least one vitamin. According to certain embodiments, the hyaluronan composition comprises a therapeutically effective amount of hyaluronan and a nutritionally effective amount of more than one different vitamin. According to certain embodiments, the hyaluronan composition comprises a therapeutically effective amount of hyaluronan and a nutritionally effective amount of at least one mineral. According to certain embodiments, the hyaluronan composition comprises a therapeutically effective amount of hyaluronan and a nutritionally effective amount of more than one different mineral. According to certain embodiments, the hyaluronan composition comprises a therapeutically effective amount of hyaluronan and a nutritionally effective amount of at least one vitamin and at least one mineral. According to certain embodiments, the hyaluronan composition comprises a therapeutically effective amount of hyaluronan and a nutritionally effective amount of more than one different vitamin and at least one mineral. According to certain embodiments, the hyaluronan composition comprises a therapeutically effective amount of hyaluronan and a nutritionally effective amount of at least one vitamin and more than one different mineral. According to certain embodiments, the hyaluronan composition comprises a therapeutically effective amount of hyaluronan and a nutritionally effective amount of more than one different vitamin and more than one different mineral.

The hyaluronan composition may also include a drug component alone or in addition to the nutritional supplemental.

EXAMPLES

The following examples are provided to further illustrate the hyaluronan composition and method of administering the exogenous hyaluronan to vertebrate subjects. It should be noted that the examples are provided for illustration and should not be construed to limit the scope of the composition or method of administering the composition in any manner.
Bone Remodeling/Osteophyte Formation A study was designed and conducted to examine the effect of an orally administered exogenous hyaluronan biopolymer to prevent poor bone remodeling and osteophyte development. A total of 10 inbred laboratory mice were obtained and housed according to accepted laboratory animal standards. The mice underwent an aggressive knee instability surgery. The medial collateral and anterior cruciate ligaments were identified and transected followed by a partial meniscectomy.

Following surgery mice were randomly assigned to two groups. Control Group (N=5) were gavaged 5 days/week for 4 weeks with saline. Treatment Group (N=5) was gavaged 5 days/week with MHB3™ hyaluronan formulation (Cogent Solutions Group LLC, Lexington, Ky.) at a dose of 10 mg/kg, for five weeks. During the five weeks post-surgery, it was anticipated that all animals would have severe bone remodeling and osteophyte development. After five weeks of treatment the mice were euthanized, their knees decalcified, paraffin embedded, stained with Saffrin-O and evaluated on slides.

As shown in the tissue sample of FIG. 1 (Control Mouse), the red-staining tissue with poorly defined margins on the interior of the bone tissue is indicative of a failed attempt to remodel the bone and the formation of osteophytes leading to severe instability. On the other hand, the tissue sample of FIG. 2 (Treatment Mouse) which was orally administered the hyaluronan composition exhibits well-defined bright red-staining tissue on the surface of the bone. The well-defined margins of red-staining tissue are indicative of intake and healthy bone surfaces without the formation of osteophytes. These results demonstrate the effectiveness of the oral administration of therapeutically effective amounts of an exogenous hyaluronan biopolymer to mice having undergone knee instability surgery, as compared to those mice receiving a control composition comprising normal saline.

This is the first time, to our knowledge, that an orally administered, exogenous hyaluronan biopolymer has been shown to have bone protecting benefits including but not limited osteophyte prevention.

Likewise, through parenteral administration of a buffered hyaluronan solution, such as through subcutaneous or intramuscular administration, similar effects are observed. It will be apparent to those skilled in the art to which the present invention pertains how to make and how to use such a buffered hyaluronan solution for parenteral administration.

While the method for administering hyaluronan to vertebrate subject has been described above in connection with certain illustrative embodiments, it is to be understood that other embodiments may be used or modifications and additions may be made to the described embodiments for performing the same function without deviating therefrom. Furthermore, all embodiments disclosed are not necessarily in the alternative, as various embodiments may be combined to provide the desired characteristics. Variations can be made by one having ordinary skill in the art without departing from the spirit and scope of the disclosed method. Therefore, the method should not be limited to any single embodiment, but rather construed in breadth and scope in accordance with the recitation of the attached claims. Equivalents will be readily apparent to those skilled in the art.

I claim:

1. A method for slowing, attenuating, mitigating, and/or ameliorating the formation of osteophytes in a vertebrate subject, the method comprising orally administering a composition comprising a therapeutically effective amount of liquid hyaluronan to the subject.

2. The method of claim 1, wherein the composition comprises from about 0.2 to about 5 mg hyaluronan per kg body weight of the subject per day.

3. The method of claim 2, wherein the composition comprises from about 0.4 to about 4 mg hyaluronan per kg body weight of the subject per day.

4. The method of claim 3, wherein the composition comprises from about 0.6 to about 3 mg hyaluronan per kg body weight of the subject per day.

5. The method of claim 4, wherein the composition comprises from about 0.8 to about 2 mg hyaluronan per kg body weight of the subject per day.

6. The method of claim 5, wherein the composition comprises about 1 mg hyaluronan per kg body weight of the subject per day.

7. The method of claim 1, wherein the composition further comprises at least one pharmaceutically acceptable excipient.

8. The method of claim 7, wherein the composition comprises water.

9. The method of claim 8, wherein the composition comprises sodium chloride.

10. The method of claim 8, wherein the composition comprises citric acid.

11. The method of claim 7, wherein the composition comprises an antimicrobial preservative selected from potassium sorbate, sodium benzoate, and mixtures thereof.

12. The method of claim 1, wherein the hyaluronan is polydisperse comprising molecular weights from about 500,000 to about 2,500,000 Daltons.

13. The method of claim 12, wherein the hyaluronan is polydisperse comprising molecular weights from about 750,000 to about 2,250,000 Daltons.

14. The method of claim 13, wherein the hyaluronan is polydisperse comprising molecular weights from about 1,000,000 to about 2,000,000 Daltons.

15. The method of claim 14, wherein the hyaluronan is polydisperse comprising molecular weights from about 1,250,000 to about 1,750,000 Daltons.

16. The method of claim 15, wherein the hyaluronan is polydisperse comprising molecular weights from about 1,375,000 to about 1,625,000 Daltons.

17. The method of claim 16, wherein the hyaluronan is of median molecular weight about 1,500,000 Daltons.

18. The method of claim 1, wherein the hyaluronan is a product of microbial fermentation.

19. The method of claim 1, wherein the subject is selected from a human subject, an equine subject, a canine subject, or a feline subject.

20. The method of claim 1, wherein the formation of osteophytes is a result of injury.

21. The method of claim 1, wherein the formation of osteophytes is a result of a process other than injury.

22. The method of claim 1, wherein the pH of the composition is between about 3.5 and about 7.

23. The method of claim 1, wherein the pH of the composition is between about 4.5 and about 7.

24. The method of claim 1, wherein the pH of the composition is between about 5.5 and about 7.

25. The method of claim 1, wherein the pH of the composition is between about 2.5 and about 5.5.

26. The method of claim 1, wherein the pH of the composition is between about 2.5 and about 4.5.

27. The method of claim 1, wherein the pH of the composition is between about 4.5 and about 5.5.

28. A method for slowing, attenuating, mitigating, and/or ameliorating the formation of osteophytes in a vertebrate subject, the method comprising administering a composition consisting essentially of a therapeutically effective amount of liquid hyaluronan to the subject.

29. A method for slowing, attenuating, mitigating, and/or ameliorating the formation of osteophytes in a vertebrate subject, the method comprising orally administering a composition consisting essentially of a therapeutically effective amount of liquid hyaluronan to the subject, wherein the hyaluronan is polydisperse comprising molecular weights from about 500,000 to about 2,500,000 Daltons.

* * * * *